(12) United States Patent
Strebelle et al.

(10) Patent No.: US 7,732,649 B2
(45) Date of Patent: *Jun. 8, 2010

(54) PROCESS FOR THE MANUFACTURING OF 1,2-DICHLOROETHANE

(75) Inventors: Michel Strebelle, Brussels (BE); Dominique Balthasart, Brussels (BE)

(73) Assignee: SOLVAY (Societe Anonyme), Brussels (BE)

( * ) Notice: Subject to any disclaimer, the term of this patent is extended or adjusted under 35 U.S.C. 154(b) by 130 days.

This patent is subject to a terminal disclaimer.

(21) Appl. No.: 11/722,603

(22) PCT Filed: Dec. 21, 2005

(86) PCT No.: PCT/EP2005/057041

§ 371 (c)(1),
(2), (4) Date: Nov. 2, 2007

(87) PCT Pub. No.: WO2006/067188

PCT Pub. Date: Jun. 29, 2006

(65) Prior Publication Data

US 2008/0207968 A1 Aug. 28, 2008

(30) Foreign Application Priority Data

Dec. 23, 2004 (FR) .................... 04 13873
Apr. 1, 2005 (FR) .................... 05 03252

(51) Int. Cl.
*C07C 17/00* (2006.01)
(52) U.S. Cl. .................... 570/223; 570/224; 570/244; 526/62
(58) Field of Classification Search .................... 570/244, 570/223, 224; 526/62
See application file for complete search history.

(56) References Cited

U.S. PATENT DOCUMENTS 5,789,499 A * 8/1998 Masuko et al. .................. 526/62

(Continued)

FOREIGN PATENT DOCUMENTS

DE 1 443 707 12/1968

(Continued)

OTHER PUBLICATIONS

U.S. Appl. No. 12/304,297, filed Dec. 11, 2008, Balthasart, et al.

(Continued)

*Primary Examiner*—Jafar Parsa
*Assistant Examiner*—Yate' K Cutliff
(74) *Attorney, Agent, or Firm*—Oblon, Spivak, McClelland, Maier & Neustadt, L.L.P.

(57) ABSTRACT

Process for the manufacture of 1,2-dichloroethane starting with a hydrocarbon source according to which: a) the hydrocarbon source is subjected to cracking which produces a mixture of products containing ethylene and other constituents; b) the said mixture of products is separated into a fraction enriched with compounds which are lighter than ethylene, containing part of the ethylene (fraction A), into a fraction enriched with ethylene (fraction B) and into a heavy fraction (fraction C); c) fraction A is conveyed to a chlorination reactor and fraction B to an oxychlorination reactor, in which reactors most of the ethylene present in fractions A and B is converted to 1,2-dichloroethane; d) the 1,2-dichloroethane obtained is separated from the streams of products derived from the chlorination and oxychlorination reactors.

12 Claims, 4 Drawing Sheets

U.S. PATENT DOCUMENTS

| | | | |
|---|---|---|---|
| 2004/0267063 A1* | 12/2004 | Harth et al. | 570/224 |
| 2007/0142682 A1 | 6/2007 | Strebelle et al. | |
| 2007/0161830 A1 | 7/2007 | Strebelle | |

FOREIGN PATENT DOCUMENTS

| | | |
|---|---|---|
| EP | 0 883 588 | 12/1998 |
| GB | 970961 | 7/1963 |
| GB | 1096594 | 3/1965 |
| WO | WO 00/26164 | 5/2000 |
| WO | WO 03/048088 | 6/2003 |

OTHER PUBLICATIONS

U.S. Appl. No. 12/304,329, filed Dec. 11, 2008, Strebelle, et al.
U.S. Appl. No. 12/304,379, filed Dec. 11, 2008, Balthasart, et al.
U.S. Appl. No. 12/304,434, filed Dec. 11, 2008, Strebelle, et al.
U.S. Appl. No. 11/722,587, filed Jun. 22, 2007, Strebelle, et al.
U.S. Appl. No. 11/722,589, filed Jun. 22, 2007, Balthasart, et al.
U.S. Appl. No. 11/722,598, filed Jun. 22, 2007, Strebelle, et al.
U.S. Appl. No. 11/722,607, filed Jun. 22, 2007, Strebelle, et al.

* cited by examiner

PROCESS FOR THE MANUFACTURING OF 1,2-DICHLOROETHANE

This application is a 371 of PCT/EP05/57041, filed Dec. 21, 2005.

The present invention relates to a process for the manufacture of 1,2-dichloroethane (DCE), a process for the manufacture of vinyl chloride (VC) and a process for the manufacture of polyvinyl chloride (PVC).

To date, ethylene which is more than 99.8% pure is normally used for the manufacture of DCE. This ethylene of very high purity is obtained via the cracking of various petroleum products, followed by numerous complex and expensive separation operations in order to isolate the ethylene from the other products of cracking and to obtain a product of very high purity.

Given the high cost linked to the production of ethylene of such high purity, various processes for the manufacture of DCE using ethylene having a purity of less than 99.8% have been developed. These processes have the advantage of reducing the costs by simplifying the course of separating the products resulting from the cracking and by thus abandoning complex separations which are of no benefit for the manufacture of DCE.

For example, patent application WO 00/26164 describes a process for the manufacture of DCE by simplified cracking of ethane coupled with chlorination of ethylene. To this effect, an ethylene chlorination step takes place in the presence of the impurities obtained during the cracking of the ethane.

Patent application WO 03/48088 describes, for its part, a process for the manufacture of DCE by dehydrogenation of ethane, giving rise to the formation of a fraction comprising ethane, ethylene and impurities including hydrogen, which fraction is then subjected to chlorination and/or oxychlorination.

The processes described have nevertheless the disadvantage that the ethylene obtained cannot be used for an ethylene chlorination/oxychlorination process given that the ethylene contains impurities whose presence during the oxychlorination reaction could cause problems of exploitation, namely a poisoning of the catalyst with heavy products and an uneconomical conversion of the hydrogen present. This conversion of hydrogen would consume oxygen and would release a large heat of reaction. This would then limit the capacity of the oxychlorination reactor, which is generally linked to the heat exchange capacity. An unusually high investment must therefore be made in order to ensure the heat exchange surface area, and thereby the reactor volume, induced by the presence of hydrogen in the mixture. The adopted option of burning the hydrogen in a separator reactor does not resolve the difficulty because it requires a large quantity of oxygen because it is stoichiometric with respect to the hydrogen, and a large surface area for exchange in order to eliminate this heat of combustion, its consequence is a significant consumption of ethylene and it can have problems linked to safety. Finally, the removal of the water formed causes an increase in the production costs.

The aim of the present invention, for its part, is to provide a process using ethylene with a purity of less than 99.8% which has the advantage of reducing the costs by abandoning complex separations for isolating the ethylene from the other products of cracking which are of no benefit for the manufacture of DCE, and which has the advantage of avoiding the abovementioned problems.

To this effect, the invention relates to a process for the manufacture of DCE starting with a hydrocarbon source according to which:

a) the hydrocarbon source is subjected to cracking which produces a mixture of products containing ethylene and other constituents;
b) the said mixture of products is separated into a fraction enriched with compounds which are lighter than ethylene, containing part of the ethylene (fraction A), into a fraction enriched with ethylene (fraction B) and into a heavy fraction (fraction C);
c) fraction A is conveyed to a chlorination reactor and fraction B to an oxychlorination reactor, in which reactors most of the ethylene present in the fractions A and B is converted to DCE;
d) the DCE obtained is separated from the streams of products derived from the chlorination and oxychlorination reactors.

The hydrocarbon source considered may be any known hydrocarbon source. Preferably, the hydrocarbon source subjected to cracking (step a)) is chosen from the group consisting of naphtha, gas oil, natural gas liquid, ethane, propane, butane, isobutane and mixtures thereof. In a particularly preferred manner, the hydrocarbon source is chosen from the group consisting of ethane, propane and propane/butane mixtures. Good results were obtained with a hydrocarbon source chosen from the group consisting of propane and propane/butane mixtures. The propane/butane mixtures may exist as such or may consist of mixtures of propane and butane.

The expression ethane, propane, butane and propane/butane mixtures is understood to mean, for the purposes of the present invention, products that are commercially available, namely that consist mainly of the pure product (ethane, propane, butane or propane/butane as a mixture) and secondarily of other saturated or unsaturated hydrocarbons, which are lighter or heavier than the pure product itself.

The expression cracking (step a)) is understood to mean, for the purposes of the present invention, all the steps for treating the hydrocarbon source which lead to the formation of a mixture of products containing ethylene and other constituents which will be separated into the fractions A, B and C in step b) of the process according to the invention.

Such a cracking may be carried out according to any known technique as long as it allows the production of a mixture of products containing ethylene and other constituents. Advantageously, the cracking comprises a first step of pyrolysis (that is to say a conversion under the action of heat) of the hydrocarbon source in the presence or absence of third compounds such as water, oxygen, a sulphur derivative and/or a catalyst. This first step is preferably followed by steps for thermal recovery of the heat of the cracked gases, for separating the heavy products (for example via organic quenching and aqueous quenching), for compressing and drying the gases and for removing most of the carbon dioxide and most of the sulphur compounds present or added (for example by means of an alkaline wash), optionally for hydrogenating the undesirable derivatives such as for example acetylene and optionally the removal of part of the hydrogen and/or of the methane, for example via a PSA (pressure swing adsorption) process or via a membrane process. The steps for hydrogenating the undesirable derivatives and for removing part of the hydrogen and/or of the methane may be carried out during step b) below (for example during the first step for separating the mixture of products derived from step a) or on fraction A). Preferably, these steps are carried out during step a) for cracking.

Advantageously, in the process according to the invention, the mixture of products containing ethylene and other constituents derived from step a) comprises hydrogen, methane, compounds comprising from 2 to 7 carbon atoms, carbon monoxide, nitrogen and oxygen. The hydrogen, the methane and the compounds comprising from 2 to 7 carbon atoms other than acetylene are preferably present in an amount of at least 200 ppm by volume relative to the total volume of the said mixture of products. The carbon monoxide, the nitrogen, the oxygen and the acetylene may be present in an amount of less than 200 ppm by volume or in an amount of at least 200 ppm by volume relative to the total volume of the said mixture of products. Compounds containing more than 7 carbon atoms, carbon dioxide, hydrogen sulphide and other sulpho compounds and water may also be present in the abovementioned mixture of products in an amount of less than 200 ppm by volume relative to the total volume of the said mixture of products.

After step a) for cracking defined above, the mixture of products containing ethylene and other constituents is subjected to step b) which advantageously comprises a maximum of four, preferably a maximum of three separation steps in order to obtain the two fractions containing ethylene, namely fraction A and fraction B.

According to the process according to the invention, fraction A is advantageously conveyed to the chlorination reactor and fraction B advantageously to the oxychlorination reactor, preferably after expansion with recovery of energy.

According to the process of the invention, the quantities defined below to characterize the fraction B and the fraction A are those before their respective entry into oxychlorination and into chlorination.

Fraction B is advantageously characterized by a hydrogen content of less than or equal to 2%, preferably of less than or equal to 0.5% and in a particularly preferred manner of less than or equal to 0.1% by volume relative to the total volume of fraction B.

Fraction B is characterized by a content of compounds containing at least 3 carbon atoms, advantageously less than or equal to 0.01%, preferably less than or equal to 0.005% and in a particularly preferred manner less than or equal to 0.001% by volume relative to the total volume of fraction B.

Fraction B advantageously contains from 40% to 99.5% by volume of ethylene relative to the total volume of fraction B. Fraction B advantageously contains at least 40%, preferably at least 50% and in a particularly preferred manner at least 60% by volume of ethylene relative to the total volume of fraction B. Fraction B advantageously contains at most 99.5%, preferably at most 99.2% and in a particularly preferred manner at most 99% by volume of ethylene relative to the total volume of fraction B.

In the preferred case where the hydrocarbon source is ethane, fraction B advantageously comprises at least 60%, preferably at least 70% and in a particularly preferred manner at least 75% by volume of ethylene relative to the total volume of fraction B. Fraction B advantageously comprises at most 99.5%, preferably at most 99.2% and in a particularly preferred manner at most 99% by volume of ethylene relative to the total volume of fraction B.

In the preferred case where the hydrocarbon source is a propane/butane mixture, fraction B advantageously comprises at least 40%, preferably at least 50% and in a particularly preferred manner at least 60% by volume of ethylene relative to the total volume of fraction B. Fraction B advantageously comprises at most 99.5%, preferably at most 99.2% and in a particularly preferred manner at most 99% by volume of ethylene relative to the total volume of fraction B.

Fraction B is additionally characterized by an acetylene content which is advantageously less than or equal to 0.01%, preferably less than or equal to 0.005% and in a particularly preferred manner less than or equal to 0.001% by volume relative to the total volume of fraction B.

Fraction A is enriched with compounds which are lighter than ethylene. These compounds are generally methane, nitrogen, oxygen, hydrogen and carbon monoxide. Advantageously, fraction A contains at least 70%, preferably at least 80% and in a particularly preferred manner at least 85% of compounds lighter than ethylene which are contained in the mixture of products subjected to step b). Advantageously, fraction A contains at most 99.99%, preferably at most 99.97% and in a particularly preferred manner at most 99.95% of compounds lighter than ethylene which are contained in the mixture of products subjected to step b).

In the preferred case where the hydrocarbon source is ethane, fraction A contains at least 90%, preferably at least 95% and in a particularly preferred manner at least 98% of compounds lighter than ethylene which are contained in the mixture of products subjected to step b). Advantageously, fraction A contains at most 99.99%, preferably at most 99.98% and in a particularly preferred manner at most 99.97% of compounds lighter than ethylene which are contained in the mixture of products subjected to step b).

In the preferred case where the hydrocarbon source is a propane/butane mixture, fraction A contains at least 70%, preferably at least 80% and in a particularly preferred manner at least 85% of compounds lighter than ethylene which are contained in the mixture of products subjected to step b). Advantageously, fraction A contains at most 99.99%, preferably at most 99.95% and in a particularly preferred manner at most 99.9% of compounds lighter than ethylene which are contained in the mixture of products subjected to step b).

Fraction A is characterized by a content of compounds containing at least 3 carbon atoms, advantageously less than or equal to 0.01%, preferably less than or equal to 0.005% and in a particularly preferred manner less than or equal to 0.001% by volume relative to the total volume of fraction A.

Fraction A advantageously contains a content by volume of ethylene such that it represents from 10% to 90% of the content by volume of ethylene of fraction B. Fraction A advantageously contains a content by volume of ethylene such that it is less than or equal to 90%, preferably less than or equal to 85% and in a particularly preferred manner less than or equal to 80% of the content by volume of ethylene of fraction B. Fraction A advantageously contains a content by volume of ethylene such that it is at least 10%, preferably at least 15% and in a particularly preferred manner at least 20% of the content by volume of ethylene of fraction B.

In the preferred case where the hydrocarbon source is ethane, fraction A advantageously contains a content by volume of ethylene such that it is less than or equal to 90%, preferably less than or equal to 85% and in a particularly preferred manner less than or equal to 80% of the content by volume of ethylene of fraction B. Fraction A advantageously contains a content by volume of ethylene such that it is at least 15%, preferably at least 20% and in a particularly preferred manner at least 22% of the content by volume of ethylene of fraction B.

In the preferred case where the hydrocarbon source is a propane/butane mixture, fraction A advantageously contains a content by volume of ethylene such that it is less than or equal to 80%, preferably less than or equal to 75% and in a particularly preferred manner less than or equal to 70% of the content by volume of ethylene of fraction B. Fraction A advantageously contains a content by volume of ethylene such that it is at least 10%, preferably at least 15% and in a particularly preferred manner at least 20% of the content by volume of ethylene of fraction B.

Fraction A is additionally characterized by an acetylene content which is advantageously less than or equal to 0.01%, preferably less than or equal to 0.005% and in a particularly preferred manner less than or equal to 0.001% by volume relative to the total volume of fraction A.

According to a first variant of the process according to the invention, considering that the process for the manufacture of DCE is advantageously balanced (that is to say that the process of manufacture by chlorination and oxychlorination of ethylene and pyrolysis of the 1,2-dichloroethane (DCE) formed makes it possible to generate the quantity of HCl necessary for the process), the fraction by weight of the ethylene throughput in each of fractions A and B is advantageously between 45 and 55% of the total quantity of ethylene produced (fraction A+fraction B). Preferably, the fraction by weight of the throughput of ethylene in fraction A is of the order of 55% and the fraction by weight of the throughput of ethylene in fraction B is of the order of 45% of the total quantity produced. In a particularly preferred manner, the fraction by weight of the throughput of ethylene in fraction A is of the order of 52.5% and the fraction by weight of the throughput of ethylene in fraction B is of the order of 47.5% of the total quantity produced.

According to a second variant of the process according to the invention, considering that the process for the manufacture of DCE is advantageously unbalanced (that is to say for example that an external source of HCl makes it possible to provide part of the supply of HCl for the oxychlorination or that a fraction of the DCE produced is not subjected to pyrolysis), the fraction by weight of the throughput of ethylene in each of fractions A and B is advantageously between 20 and 80% of the total quantity of ethylene produced (fraction A+fraction B). Preferably, the fraction by weight of the throughput of ethylene in fraction A is between 25 and 75% of the total quantity of ethylene produced (fraction A+fraction B).

According to a first embodiment of the second variant of the process according to the invention, considering that the process for the manufacture of DCE is advantageously unbalanced by an external source of HCl, the fraction by mole of the throughput of ethylene in fraction A is advantageously between 45 and 55%, preferably between 50 and 54% and in a particularly preferred manner of the order of 52.5% of the difference between the total molar quantity of ethylene contained in the mixture of products subjected to step b) and the molar quantity of HCl of the external source.

According to a second embodiment of the second variant of the process according to the invention, considering that the process for the manufacture of DCE is advantageously unbalanced by a co-production of DCE (some of the DCE is therefore not subjected to pyrolysis), the fraction by mole of the throughput of ethylene in fraction B is advantageously between 45 and 55%, preferably between 46 and 50% and in a particularly preferred manner of the order of 47.5% of the difference between the total molar quantity of ethylene contained in the mixture of products subjected to step b) and the molar quantity of DCE co-produced.

According to the process of the invention, during step b), the mixture of products is separated into a fraction enriched with the compounds lighter than ethylene containing some of the ethylene (fraction A), into a fraction enriched with ethylene (fraction B) and into a heavy fraction (fraction C). Fraction C advantageously contains ethane and compounds comprising at least 3 carbon atoms. Advantageously, these compounds comprising at least 3 carbon atoms result from the mixture of products containing ethylene and other constituents derived from step a) or are generated by side reactions during step b). Among the compounds comprising at least 3 carbon atoms, there may be mentioned propane, propene, butanes and their unsaturated derivatives as well as all the saturated or unsaturated heavier compounds.

After production during step b), according to a first case, fraction C is advantageously subjected to a hydrogenation step, preferably followed by a step of separation, for example by distillation, into two different fractions respectively containing compounds comprising less than 5 carbon atoms, for one of them, and compounds comprising at least 5 carbon atoms for the other. This separation step is in a particularly preferred manner followed by recycling of the compounds comprising less than 5 carbon atoms to the cracking step. The compounds comprising at least 5 carbon atoms are for their part, in a most particularly preferred manner, burnt in order to provide energy or upgraded in any form.

According to a second case, a separation step consisting of the separation of fraction C, for example by distillation, into two different fractions respectively containing compounds comprising less than 5 carbon atoms, for one of them, and compounds comprising at least 5 carbon atoms for the other, is advantageously carried out. The resulting fraction containing the compounds comprising less than 5 carbon atoms is then preferably subjected to a hydrogenation step before recycling to the cracking step. As for the compounds comprising at least 5 carbon atoms, they are in a particularly preferred manner burnt in order to provide energy or upgraded in any form.

The first case set out above is preferred.

According to a first embodiment of the process according to the invention, the mixture of products derived from step a) is advantageously subjected to a first separation step called step S1 and to a second separation step called step S1' in order to obtain the two fractions containing ethylene, namely fraction A and fraction B.

Step S1 advantageously consists in the separation of the mixture of products derived from step a) inside a main column (called column C1) into three different fractions, namely fraction A which leaves at the top of column C1, fraction C which leaves at the bottom of column C1 and a fraction (called fraction F1) which is drawn off from the side of column C1.

Step S1' advantageously consists in separating fraction F1 into two different fractions, namely a fraction F1' which is conveyed to the column C1 and fraction B.

According to the first embodiment of the process according to the invention, step b) therefore preferably comprises:
  a first separation step S1 which consists in the separation of the said mixture of products inside a main column C1 into fraction A at the top of column C1, into fraction C at the bottom of column C1 and into fraction F1 drawn off from the side of column C1, and
  a second separation step S1' which consists in the separation of fraction F1 into a fraction F1' which is conveyed to the column C1 and into fraction B.

In a particularly preferred manner, step b) comprises only the two steps mentioned above.

Prior to its introduction into column C1, the mixture of products derived from step a) may be subjected to a heat conditioning step. The expression heat conditioning step is understood to mean a succession of heat exchanges optimizing the use of energy, for example the gradual cooling of the mixture of products in a train of exchangers first cooled with untreated water, and then with ice-cold water and then with increasingly cooled fluids plus cross exchangers recovering the sensible heat of the streams produced.

The said mixture of products may be introduced into the column C1 during step S1 as a single fraction or as several subfractions. It is preferably introduced as several subfractions.

The main column C1 is advantageously a column comprising a stripping section and/or a rectifying section. If the two sections are present, the rectifying section preferably surmounts the stripping section.

The column C1 is advantageously chosen from distillation columns comprising the abovementioned two sections and the columns containing only one of the two sections. Preferably, the column C1 is a distillation column.

Step S1 is therefore preferably a distillation step.

The column C1 is advantageously provided with the associated auxiliary equipment such as for example at least one reboiler and at least one condenser. Devices allowing intermediate drawing off and an intermediate heat exchange may be added to the main column.

Fraction A enriched with the most volatile compounds advantageously leaves at the top of column C1 whereas fraction C enriched with the least volatile compounds advantageously leaves at the bottom of column C1.

As for fraction F1, it is advantageously drawn off from the side of the column C1 by collecting liquid or steam circulating in the column. The drawing off is preferably performed on the liquid.

The drawing off may be performed in the stripping section or in the rectifying section of the column. It is preferably performed in the rectifying section. A drawing off in the central third of the rectifying section is particularly preferred. The drawing off of liquid in the central third of the rectifying section is most particularly preferred.

The abovementioned step S1 is advantageously performed at a pressure of at least 15, preferably of at least 20 and in a particularly preferred manner of at least 25 bar. Step S1 is advantageously performed at a pressure of at most 45, preferably of at most 40 and in a particularly preferred manner of at most 38 bar.

The temperature at which step S1 is performed is advantageously at least −70, preferably at least −65 and in a particularly preferred manner at least −60° C. at the top of column C1. It is advantageously at most −30, preferably at most −40 and in a particularly preferred manner at most −50° C. at the top of column C1.

In the case where the hydrocarbon source is ethane, the temperature at the bottom of column C1 is advantageously at least −10, preferably at least 0 and in a particularly preferred manner at least 5° C. It is advantageously at most 40, preferably at most 30 and in a particularly preferred manner at most 25° C.

In the case where the hydrocarbon source is a propane/butane mixture, the temperature at the bottom of column C1 is advantageously at least 30, preferably at least 40 and in a particularly preferred manner at least 50° C. It is advantageously at most 100, preferably at most 90 and in a particularly preferred manner at most 80° C.

The fraction F1 drawn off from the side of the column C1 is advantageously subjected to the separation step S1' so as to be separated into two different fractions, namely a fraction F1' which is conveyed to the column C1 and fraction B.

Fraction F1 may be drawn off from the column C1 in the liquid state or in the gaseous state.

If the fraction F1 is drawn off in the liquid state, it may be conveyed to an evaporator or to an auxiliary column C1'.

In the case where the fraction F1 is conveyed to an evaporator, part of fraction F1, in the form of a fraction F1', is advantageously evaporated and recycled to the main column C1 while the other part is advantageously extracted from the evaporator thus constituting fraction B. As a variant, fraction F1 may also be partially vaporized in order to produce fraction B, the balance, in the form of a fraction F1', being recycled to the column C1.

In the case where the fraction F1 is conveyed to an auxiliary column C1', the auxiliary column C1' is preferably a stripping column, namely a column which comprises only one stripping section. The auxiliary column C1' is advantageously provided with associated auxiliary equipment, preferably a reboiler. Fraction B is advantageously extracted therefrom and the balance of fraction F1, in the form of a fraction F1' which is then a stream concentrated with impurities more volatile than ethylene ($H_2$, $CO$, $N_2$, $O_2$ and $CH_4$), is advantageously conveyed to the column C1.

If the fraction F1 is drawn off in the liquid state, it is preferably conveyed to an auxiliary column C1' which is preferably a stripping column. Step S1' is then in this case preferably a stripping step.

If the fraction F1 is drawn off in the gaseous state, it may be conveyed to a condenser or to an auxiliary column C1'.

In the case where the fraction F1 is conveyed to a condenser, part of fraction F1, in the form of a fraction F1', is advantageously condensed and recycled to the main column C1 while the other part is advantageously extracted from the condenser thus constituting the fraction B. As a variant, the fraction F1 may also be partially condensed in order to produce the fraction B, the balance, in the form of a fraction F1', being recycled to the column C1.

In the case where the fraction F1 is conveyed to an auxiliary column C1', the auxiliary column C1' is preferably a rectifying column, namely a column which comprises only a rectifying section. The auxiliary column C1' is advantageously provided with associated auxiliary equipment, preferably a condenser. The fraction B is advantageously extracted therefrom and the balance of the fraction F1 in the form of a fraction F1' which is then a stream concentrated with impurities less volatile than ethylene (ethane, compounds containing at least 3 carbon atoms), is advantageously conveyed to the column C1.

If the fraction F1 is drawn off in the gaseous state, it is preferably conveyed to an auxiliary column C1' which is preferably a rectifying column. Step S1' is then in this case preferably a rectifying step.

According to the first embodiment of the process according to the invention, a most particular preference is given to the case where the fraction F1 is conveyed to an auxiliary column C1'.

According to this most particular preference, step b) therefore comprises in a particularly preferred manner:
 a first separation step S1 which consists in the separation of the said mixture of products inside a main column C1 into fraction A at the top of column C1, into fraction C at the bottom of column C1 and into fraction F1 drawn off from the side of column C1, and
 a second separation step S1' which consists in the separation of fraction F1 inside a column C1' into a fraction F1' at the top of column C1' which is conveyed to the column C1 and into fraction B at the bottom of column C1'.

According to the first embodiment of the process according to the invention, a truly most particular preference is given to the case where the fraction F1 is drawn off from the column C1 in the liquid state and conveyed to an auxiliary column C1' which is a stripping column.

The abovementioned step S1' is then advantageously performed at a pressure of at least 15, preferably of at least 25 and in a particularly preferred manner of at least 30 bar. Step S1' is advantageously performed at a pressure of at most 45, preferably of at most 40 and in a particularly preferred manner of at most 38 bar.

The temperature at which step S1' is performed is advantageously at least −40, preferably at least −30 and in a particularly preferred manner at least −25° C. at the top of the stripping column C1'. It is advantageously at most 0, preferably at most −10 and in a particularly preferred manner at most −15° C. at the top of column C1'.

The temperature at the bottom of the stripping column C1' is at least −30, preferably at least −20 and in a particularly preferred manner at least −15° C. It is advantageously at most 20, preferably at most 15 and in a particularly preferred manner at most 10° C.

According to the first embodiment of the process according to the invention, fraction B is advantageously conveyed to the oxychlorination reactor, preferably after evaporation and expansion if fraction F1 is drawn off in the liquid state or after expansion if fraction F1 is drawn off in the gaseous state, in both cases advantageously with energy recovery. In a particularly preferred manner, fraction B is conveyed to the oxychlorination reactor after evaporation and expansion in the case where fraction F1 is drawn off in the liquid state, advantageously with energy recovery.

A preferred subvariant of the first embodiment of the process according to the invention is to carry out the separation step S1' by means of an auxiliary column C1' identical to the main column C1, both columns being optionally thermally integrated and operating at different pressures; the condenser of one serving as the reboiler to the other.

According to a second embodiment of the process according to the invention, the mixture of products derived from step a) is advantageously subjected to a first separation step called step S2, to a second separation step called step S2' and to a third separation step called step S2" in order to obtain the two fractions containing ethylene, namely fraction A and fraction B.

Step S2 advantageously consists in the separation of the mixture of products derived from step a) in a main column (called column C2) into two different fractions, namely a fraction F2 which leaves at the top of column C2 and fraction C which leaves at the bottom of column C2.

Step S2' advantageously consists in the separation of fraction F2 into two different fractions, namely fraction A and a fraction F2'.

Step S2" advantageously consists in the separation of fraction F2' into two different fractions, namely fraction B and a fraction F2".

According to the second embodiment of the process according to the invention, step b) therefore preferably comprises:
 a first separation step S2 which consists in the separation of the said mixture of products in a main column C2 into a fraction F2 at the top of column C2 and into fraction C at the bottom of column C2,
 a second separation step S2' which consists in the separation of fraction F2 into fraction A and into a fraction F2', and
 a third separation step S2" which consists in the separation of fraction F2' into fraction B and into a fraction F2".

In a particularly preferred manner, step b) comprises only the three steps mentioned above.

Prior to its introduction into the column C2, the mixture of products derived from step a) may be subjected to a heat conditioning step. The expression heat conditioning step is understood to mean a succession of heat exchanges optimizing the use of energy, for example the gradual cooling of the mixture of products in a train of exchangers first cooled with untreated water, then with ice-cold water and then with increasingly cold fluids plus cross exchangers recovering the sensible heat of the streams produced.

The said mixture of products may be introduced into the column C2 during step S2 as a single fraction or as several subfractions. It is preferably introduced as several subfractions.

The main column C2 is advantageously a column comprising a stripping section and/or a rectifying section. If the two sections are present, the rectifying section preferably surmounts the stripping section.

The column C2 is advantageously chosen from distillation columns comprising the abovementioned two sections and columns comprising only one of the two sections. Preferably, the column C2 is a distillation column.

Step S2 is therefore preferably a distillation step.

The column C2 is advantageously provided with the associated auxiliary equipment such as for example at least one reboiler and at least one condenser.

The fraction F2 enriched with the most volatile compounds advantageously leaves at the top of column C2 while the fraction C enriched with the least volatile compounds advantageously leaves at the bottom of column C2.

The abovementioned step S2 is advantageously performed at a pressure of at least 15, preferably of at least 20 and in a particularly preferred manner of at least 25 bar. Step S2 is advantageously performed at a pressure of at most 45, preferably of at most 40 and in a particularly preferred manner of at most 38 bar.

The temperature at which step S2 is performed is advantageously at least −70, preferably at least −65 and in a particularly preferred manner at least −60° C. at the top of column C2. It is advantageously at most −20, preferably at most −30 and in a particularly preferred manner at most −40° C. at the top of column C2.

In the case where the hydrocarbon source is ethane, the temperature at the bottom of column C2 is advantageously at least −10, preferably at least 0 and in a particularly preferred manner at least 5° C. It is advantageously at most 40, preferably at most 30 and in a particularly preferred manner at most 25° C.

In the case where the hydrocarbon source is a propane/butane mixture, the temperature at the bottom of column C2 is advantageously at least 30, preferably at least 40 and in a particularly preferred manner at least 50° C. It is advantageously at most 100, preferably at most 90 and in a particularly preferred manner at most 80° C.

The fraction F2 which leaves at the top of column C2 is advantageously subjected to the separation step S2' so as to be separated into two different fractions, namely fraction A and a fraction F2'.

The separation step S2' is advantageously an absorption step in which fraction F2 is brought into contact with a washing agent containing DCE.

In the present description, the term "washing agent containing DCE" or more simply "washing agent" is understood to mean a composition in which the DCE is present in the liquid state.

The washing agent which may be used according to the present invention therefore advantageously contains DCE in the liquid state. The presence, in the said washing agent, of other compounds is not at all excluded from the scope of the invention. It is preferable, however, that the washing agent contains at least 50% by volume of DCE, more particularly at least 80% by volume and in a particularly preferred manner at least 95% by volume.

The washing agent used for step S2' may consist of fresh washing agent of any origin, for example crude DCE leaving the oxychlorination unit and which has not been purified, the said DCE previously purified or washing agent recovered during step S2" detailed below (fraction F2"), optionally supplemented with fresh washing agent.

Preferably, the washing agent used for step S2' consists of the fraction F2", optionally supplemented with fresh washing agent. In a particularly preferred manner, the washing agent used for step S2' consists of the fraction F2" supplemented with fresh washing agent (to compensate for the loss of washing agent during steps S2' and S2").

A major advantage of the second embodiment of the process according to the invention lies in the fact that the presence of this DCE is not at all troublesome since it is the compound mainly formed during the oxychlorination or chlorination.

The ratio between the respective throughputs of washing agent and ethylene to be extracted from the fraction F2 is not critical and can vary to a large extent. It is in practice limited only by the cost of the regeneration of the washing agent. In general, the throughput of washing agent is at least 1, preferably at least 5 and in a particularly preferred manner at least 10 tons per ton of ethylene to be extracted from the fraction F2. In general, the throughput of washing agent is at most 100, preferably at most 50 and in a particularly preferred manner at most 25 tons per ton of ethylene to be extracted from the fraction F2.

Step S2' is advantageously performed by means of an absorber such as for example a falling or rising film absorber or an absorption column C2' chosen from plate columns, packed columns, columns with structured packing, columns combining one or more of the abovementioned internals and spray columns. Step S2' is preferably performed by means of an absorption column C2' and in a particularly preferred manner by means of a plate absorption column C2'.

The column C2' is advantageously provided with associated auxiliary equipment such as, for example, at least one condenser or one cooler internal or external to the column.

The abovementioned step S2' is advantageously performed at a pressure of at least 15, preferably of at least 20 and in a particularly preferred manner at least 25 bar. Step S2' is advantageously performed at a pressure of at most 40, preferably at most 35 and in a particularly preferred manner at most 30 bar.

The temperature at which step S2' is performed is advantageously at least −10, preferably at least 0 and in a particularly preferred manner at least 10° C. at the top of the absorber or of column C2'. It is advantageously at most 60, preferably at most 50 and in a particularly preferred manner at most 40° C. at the top of the absorber or column C2'.

The temperature at the bottom of the absorber or column C2' is at least 0, preferably at least 10 and in a particularly preferred manner at least 20° C. It is advantageously at most 70, preferably at most 60 and in a particularly preferred manner at most 50° C.

The fraction F2' is advantageously subjected to the separation step S2" so as to be separated into two different fractions, namely fraction B and a fraction F2".

The separation step S2" is advantageously a desorption step in which fraction B is extracted from the washing agent.

The washing agent recovered after step S2" constituting the fraction F2" may be removed, conveyed completely or partly to the oxychlorination section or conveyed to step S2' with optional addition of fresh washing agent. Preferably, the fraction F2" is conveyed to step S2' with optional addition of fresh washing agent. In a particularly preferred manner, the fraction F2" is conveyed to step S2' with addition of fresh washing agent.

Step S2" is advantageously performed by means of a desorber such as for example a falling or rising film desorber, a reboiler or a desorption column C2" chosen from plate columns, packed columns, columns with structured packing, columns combining one or more of the abovementioned internals and spray columns. Step S2" is preferably performed by means of a desorption column C2" and in a particularly preferred manner by means of a plate desorption column C2".

The column C2" is advantageously provided with associated auxiliary equipment such as for example at least one condenser or one cooler internal or external to the column and at least one reboiler.

The abovementioned step S2" is advantageously performed at a pressure of at least 1, preferably of at least 2 and in a particularly preferred manner of at least 3 bar. Step S2" is advantageously performed at a pressure of at most 20, preferably of at most 15 and in a particularly preferred manner of at most 10 bar.

The temperature at which step S2" is performed is advantageously chosen so that more than 90%, preferably more than 95% of the ethylene contained in the fraction F2' is found in fraction B. The temperature at which step S2" is performed is advantageously at least −10, preferably at least 0 and in a particularly preferred manner at least 10° C. at the top of the desorber or of column C2". It is advantageously at most 60, preferably at most 50 and in a particularly preferred manner at most 40° C. at the top of the desorber or column C2".

The temperature at the bottom of the desorber or column C2" is at least 60, preferably at least 80 and in a particularly preferred manner at least 100° C. It is advantageously at most 200, preferably at most 160 and in a particularly preferred manner at most 150° C.

According to the second embodiment of the process according to the invention, a most particular preference is given to the case where the fraction F2 is conveyed to an absorption column C2' and the fraction F2' is conveyed to a desorption column C2".

According to this most particular preference, step b) therefore comprises in a particularly preferred manner:
- a first separation step S2 which consists in the separation of the said mixture of products in a main column C2 into a fraction F2 at the top of column C2 and into fraction C at the bottom of column C2,
- a second separation step S2' which consists in the separation of the fraction F2 in an absorption column C2' into fraction A at the top of column C2' and into a fraction F2' at the bottom of column C2', and
- a third separation step S2" which consists in the separation of the fraction F2' in a desorption column C2" into fraction B at the top of column C2" and into a fraction F2" at the bottom of column C2".

According to a third embodiment of the process according to the invention, the mixture of products derived from step a) is advantageously subjected to a first separation step called step S3 and to a second separation step called step S3' in order to obtain the two fractions containing ethylene, namely fraction A and fraction B.

Step S3 advantageously consists in the separation of the mixture of products derived from step a) in a main column (called column C3) into two different fractions, namely a fraction F3 which leaves at the top of column C3 and the fraction C which leaves at the bottom of column C3.

Step S3' advantageously consists in the separation of the fraction F3 in a column C3' into two different fractions, namely the fraction A which leaves at the top of column C3' and the fraction B which leaves at the bottom of column C3'.

According to the third embodiment of the process according to the invention, step b) therefore preferably comprises:
- a first separation step S3 which consists in the separation of the said mixture of products in a main column C3 into a fraction F3 at the top of column C3 and into fraction C at the bottom of column C3, and
- a second separation step S3' which consists in the separation of the fraction F3 in a column C3' into fraction A at the top of column C3' and into fraction B at the bottom of column C3'.

In a particularly preferred manner, step b) comprises only the two steps mentioned above.

Prior to its introduction into the column C3, the mixture of products derived from step a) may be subjected to a heat conditioning step. The expression heat conditioning step is understood to mean a succession of heat exchanges optimizing the use of energy, for example the gradual cooling of the mixture of products in a train of exchangers first cooled with untreated water, and then with ice cold water and then with increasingly cold fluids plus cross exchangers recovering the sensible heat of the streams produced.

The said mixture of products may be introduced into the column C3 during step S3 as a single fraction or as several subfractions. It is preferably introduced as several subfractions.

The main column C3 is advantageously a column comprising a stripping section and/or a rectifying section. If the two sections are present, the rectifying section preferably surmounts the stripping section.

The column C3 is advantageously chosen from distillation columns comprising the abovementioned two sections and columns containing only one of the two sections. Preferably, the column C3 is a distillation column.

Step S3 is therefore preferably a distillation step.

The column C3 is advantageously provided with the associated auxiliary equipment such as, for example, at least one reboiler and at least one condenser.

The fraction F3 enriched with the most volatile compounds advantageously leaves at the top of column C3 while the fraction C enriched with the least volatile compounds advantageously leaves at the bottom of column C3.

The abovementioned step S3 is advantageously performed at a pressure of at least 15, preferably of at least 20 and in a particularly preferred manner of at least 25 bar. The step S3 is advantageously performed at a pressure of at most 45, preferably of at most 40 and in a particularly preferred manner of at most 38 bar.

The temperature at which step S3 is performed is advantageously at least −70, preferably at least −65 and in a particularly preferred manner at least −60° C. at the top of column C3. It is advantageously at most −20, preferably at most −30 and in a particularly preferred manner at most −40° C. at the top of column C3.

In the case where the hydrocarbon source is ethane, the temperature at the bottom of column C3 is advantageously at least −10, preferably at least 0 and in a particularly preferred manner at least 5° C. It is advantageously at most 40, preferably at most 30 and in a particularly preferred manner at most 25° C.

In the case where the hydrocarbon source is a propane/butane mixture, the temperature at the bottom of column C3 is advantageously at least 30, preferably at least 40 and in a particularly preferred manner at least 50° C. It is advantageously at most 100, preferably at most 90 and in a particularly preferred manner at most 80° C.

The fraction F3 which leaves at the top of column C3 is then advantageously subjected to the separation step S3' in the column C3' so as to be separated into two different fractions, namely fraction A at the top of column C3' and fraction B at the bottom of column C3'.

The column C3' is advantageously a column comprising a stripping section and/or a rectifying section. If the two sections are present, the rectifying section preferably surmounts the stripping section.

The column C3' is advantageously chosen from the distillation columns comprising the abovementioned two sections and the columns comprising only one of the two sections. Preferably, the column C3' is a distillation column.

The step S3' is therefore preferably a distillation step.

The column C3' is advantageously provided with the associated auxiliary equipment such as, for example, at least one reboiler and at least one condenser.

The abovementioned step S3' is advantageously performed at a pressure of at least 15, preferably of at least 20 and in a particularly preferred manner of at least 25 bar. The step S3' is advantageously performed at a pressure of at most 40, preferably of at most 37 and in a particularly preferred manner of at most 35 bar.

The temperature at which the step S3' is performed is advantageously at least −70, preferably at least −67 and in a particularly preferred manner at least −65° C. at the top of column C3'. It is advantageously at most −40, preferably at most −45 and in a particularly preferred manner at most −50° C. at the top of column C3'.

The temperature at the bottom of column C3' is at least −30, preferably at least −25 and in a particularly preferred manner at least −20° C. It is advantageously at most 20, preferably at most 15 and in a particularly preferred manner at most 10° C.

According to a fourth embodiment of the process according to the invention, the mixture of products derived from step a) is advantageously subjected to a first separation step called step S4 and to a second separation step called step S4' in order to obtain the two fractions containing ethylene, namely fraction A and fraction B.

Step S4 advantageously consists in the separation of the mixture of products derived from step a) in a main column (called column C4) into two different fractions, namely fraction A which leaves at the top of column C4 and a fraction F4 which leaves at the bottom of column C4.

Step S4' advantageously consists in the separation of the fraction F4 in a column C4' into two different fractions, namely fraction B which leaves at the top of column C4' and fraction C which leaves at the bottom of column C4'.

According to the fourth embodiment of the process according to the invention, step b) therefore preferably comprises:
- a first separation step S4 which consists in the separation of the said mixture of products in a main column C4 into fraction A at the top of column C4 and into a fraction F4 at the bottom of column C4, and
- a second separation step S4' which consists in the separation of the fraction F4 in a column C4' into fraction B at the top of column C4' and into fraction C at the bottom of column C4'.

In a particularly preferred manner, step b) comprises only the two steps mentioned above.

Prior to its introduction into the column C4, the mixture of products derived from step a) may be subjected to a heat conditioning step. The expression heat conditioning step is understood to mean a succession of heat exchanges optimizing the use of energy, for example the gradual cooling of the mixture of products in a train of exchangers first cooled with untreated water, then with ice-cold water and then with increasingly cold fluids plus cross exchangers recovering the sensible heat of the streams produced.

The said mixture of products may be introduced into the column C4 during step S4 as a single fraction or as several subfractions. It is preferably introduced as several subfractions.

The main column C4 is advantageously a column comprising a stripping section and/or a rectifying section. If the two sections are present, the rectifying section preferably surmounts the stripping section.

The column C4 is advantageously chosen from the distillation columns comprising the abovementioned two sections and the columns comprising only one of the two sections. Preferably, the column C4 is a distillation column.

The step S4 is therefore preferably a distillation step.

The column C4 is advantageously provided with the associated auxiliary equipment such as, for example, at least one reboiler and at least one condenser.

The fraction A enriched with the most volatile compounds advantageously leaves at the top of column C4 while the fraction F4 enriched with the least volatile compounds advantageously leaves at the bottom of column C4.

The abovementioned step S4 is advantageously performed at a pressure of at least 15, preferably of at least 20 and in a particularly preferred manner of at least 25 bar. The step S4 is advantageously performed at a pressure of at most 45, preferably of at most 40 and in a particularly preferred manner of at most 38 bar.

The temperature at which the step S4 is performed is advantageously at least −70, preferably at least −65 and in a particularly preferred manner at least −60° C. at the top of column C4. It is advantageously at most −20, preferably at most −30 and in a particularly preferred manner at most −40° C. at the top of column C4.

In the case where the hydrocarbon source is ethane, the temperature at the bottom of column C4 is advantageously at least −10 and preferably at least −5° C. It is advantageously at most 30, preferably at most 20 and in a particularly preferred manner at most 15° C.

In the case where the hydrocarbon source is a propane/butane mixture, the temperature at the bottom of column C4 is advantageously at least 20, preferably at least 30 and in a particularly preferred manner at least 40° C. It is advantageously at most 80, preferably at most 70 and in a particularly preferred manner at most 60° C.

The fraction F4 which leaves at the bottom of column C4 is then advantageously subjected to the separation step S4' in the column C4' so as to be separated into two different fractions, namely the fraction B at the top of column C4' and the fraction C at the bottom of column C4'.

The column C4' is advantageously a column comprising a stripping section and/or a rectifying section. If the two sections are present, the rectifying section preferably surmounts the stripping section.

The column C4' is advantageously chosen from the distillation columns comprising the abovementioned two sections and the columns comprising only one of the two sections. Preferably, the column C4' is a distillation column.

The step S4' is therefore preferably a distillation step.

The column C4' is advantageously provided with the associated auxiliary equipment such as, for example, at least one reboiler and at least one condenser.

The abovementioned step S4' is advantageously performed at a pressure of at least 15, preferably of at least 20 and in a particularly preferred manner of at least 25 bar. The step S4' is advantageously performed at a pressure of at most 40, preferably of at most 37 and in a particularly preferred manner of at most 35 bar.

The temperature at which the step S4' is performed is advantageously at least −50, preferably at least −40 and in a particularly preferred manner at least −30° C. at the top of column C4'. It is advantageously at most 0, preferably at most −5 and in a particularly preferred manner at most −10° C. at the top of column C4'.

The temperature at the bottom of column C4' is at least −20, preferably at least −15 and in a particularly preferred manner at least −10° C. It is advantageously at most 20, preferably at most 15 and in a particularly preferred manner at most 10° C.

In the process according to the invention, each time the use of a distillation column is mentioned, it may be chosen from plate distillation columns, packed distillation columns, distillation columns with structured packing and distillation columns combining two or more of the abovementioned internals.

In the process according to the invention, the first, third and fourth embodiments are preferred. The third and fourth embodiments are particularly preferred and the third preferred embodiment is most particularly preferred.

The chlorination reaction is advantageously performed in a liquid phase (preferably mainly DCE) containing a dissolved catalyst such as $FeCl_3$ or another Lewis acid. It is possible to advantageously combine this catalyst with cocatalysts such as alkali metal chlorides. A pair which has given good results is the complex of $FeCl_3$ with LiCl (lithium tetrachloroferrate—as described in patent application NL 6901398).

The quantities of $FeCl_3$ advantageously used are of the order of 1 to 10 g of $FeCl_3$ per kg of liquid stock. The molar ratio of $FeCl_3$ to LiCl is advantageously of the order of 0.5 to 2.

The chlorination process according to the invention is advantageously performed at temperatures of between 30 and 150° C. Good results were obtained regardless of the pressure both at a temperature less than the boiling temperature (under-cooled chlorination) and at the boiling temperature itself (boiling chlorination).

When the chlorination process according to the invention is an under-cooled chlorination, it gave good results by operating at a temperature which is advantageously greater than or equal to 50° C. and preferably greater than or equal to 60° C., but advantageously less than or equal to 80° C. and preferably less than or equal to 70° C.; with a pressure in the gaseous phase advantageously greater than or equal to 1.5 and preferably greater than or equal to 2 absolute bar, but advantageously less than or equal to 20, preferably less than or equal to 10 and in a particularly preferred manner less than or equal to 6 absolute bar.

A boiling chlorination process is particularly preferred which makes it possible, where appropriate, to usefully recover the heat of reaction. In this case, the reaction advantageously takes place at a temperature greater than or equal to 60° C., preferably greater than or equal to 90° C. and in a particularly preferred manner greater than or equal to 95° C. but advantageously less than or equal to 150° C. and preferably less than or equal to 135° C.; with a pressure in the gaseous phase advantageously greater than or equal to 0.2, preferably greater than or equal to 0.5, in a particularly preferred manner greater than or equal to 1.2 and in a most particularly preferred manner greater than or equal to 1.5 absolute bar but advantageously less than or equal to 10 and preferably less than or equal to 6 absolute bar.

The chlorination process may also be a loop under-cooled boiling mixed chlorination process. The expression loop under-cooled boiling mixed chlorination process is understood to mean a process in which cooling of the reaction medium is performed, for example, by means of an exchanger immersed in the reaction medium or by a loop circulating in an exchanger, while producing in a gaseous phase at least the quantity of DCE formed. Advantageously, the reaction temperature and pressure are adjusted for the DCE produced to leave in the gaseous phase and to remove the remainder of the calories from the reaction medium by means of the exchange surface.

In addition, the chlorination process is advantageously performed in a chlorinated organic liquid medium. Preferably, this chlorinated organic liquid medium, also called liquid stock, mainly consists of DCE.

The fraction A containing the ethylene and the chlorine (itself pure or diluted) may be introduced by any known device into the reaction medium together or separately. A separate introduction of the fraction A may be advantageous in order to increase its partial pressure and facilitate its dissolution which often constitutes a limiting step of the process.

The chlorine is added in a sufficient quantity to convert most of the ethylene and without requiring the addition of an excess of unconverted chlorine. The chlorine/ethylene ratio used is preferably between 1.2 and 0.8 and in a particularly preferred manner between 1.05 and 0.95 mol/mol.

The chlorinated products obtained contain mainly DCE and small quantities of by-products such as 1,1,2-trichloroethane or small quantities of chlorination products of ethane or methane. The separation of the DCE obtained from the stream of products derived from the chlorination reactor is carried out according to known modes and makes it possible in general to exploit the heat of the chlorination reaction.

The unconverted products (methane, carbon monoxide, nitrogen, oxygen and hydrogen) are then advantageously subjected to an easier separation than what would have been necessary to separate pure ethylene starting with the initial mixture.

The oxychlorination reaction is advantageously performed in the presence of a catalyst comprising active elements including copper deposited on an inert support. The inert support is advantageously chosen from alumina, silica gels, mixed oxides, clays and other supports of natural origin. Alumina constitutes a preferred inert support.

Catalysts comprising active elements which are advantageously at least two in number, one of which is copper, are preferred. Among the active elements other than copper, there may be mentioned alkali metals, alkaline-earth metals, rare-earth metals and metals of the group consisting of ruthenium, rhodium, palladium, osmium, iridium, platinum and gold. The catalysts containing the following active elements are particularly advantageous: copper/magnesium/potassium, copper/magnesium/sodium; copper/magnesium/lithium, copper/magnesium/caesium, copper/magnesium/sodium/lithium, copper/magnesium/potassium/lithium and copper/magnesium/caesium/lithium, copper/magnesium/sodium/potassium, copper/magnesium/sodium/caesium and copper/magnesium/potassium/caesium. The catalysts described in patent applications EP-A 255 156, EP-A 494 474, EP-A-657 212 and EP-A 657 213, incorporated by reference, are most particularly preferred.

The copper content, calculated in metal form, is advantageously between 30 and 90 g/kg, preferably between 40 and 80 g/kg and in a particularly preferred manner between 50 and 70 g/kg of catalyst.

The magnesium content, calculated in metal form, is advantageously between 10 and 30 g/kg, preferably between 12 and 25 g/kg and in a particularly preferred manner between 15 and 20 g/kg of catalyst.

The alkali metal content, calculated in metal form, is advantageously between 0.1 and 30 g/kg, preferably between 0.5 and 20 g/kg and in a particularly preferred manner between 1 and 15 g/kg of catalyst.

The Cu:Mg:alkali metal(s) atomic ratios are advantageously 1:0.1-2:0.05-2, preferably 1:0.2-1.5:0.1-1.5 and in a particularly preferred manner 1:0.5-1:0.15-1.

Catalysts having a specific surface area, measured according to the B.E.T. method with nitrogen, advantageously between 25 $m^2/g$ and 300 $m^2/g$, preferably between 50 and 200 $m^2/g$ and in a particularly preferred manner between 75 and 175 $m^2/g$, are particularly advantageous.

The catalyst may be used in a fixed bed or in a fluidized bed. This second option is preferred. The oxychlorination process is exploited under the range of the conditions usually recommended for this reaction. The temperature is advantageously between 150 and 300° C., preferably between 200 and 275° C. and most preferably from 215 to 255° C. The pressure is advantageously greater than atmospheric pressure. Values of between 2 and 10 absolute bar gave good results. The range between 4 and 7 absolute bar is preferred. This pressure may be usefully modulated in order to obtain an optimum residence time in the reactor and to maintain a constant rate of passage for various speeds of operation. The usual residence times range from 1 to 60 s and preferably from 10 to 40 s.

The source of oxygen for this oxychlorination may be air, pure oxygen or a mixture thereof, preferably pure oxygen. The latter solution, which allows easy recycling of the unconverted reagents, is preferred.

The reagents may be introduced into the bed by any known device. It is generally advantageous to introduce the oxygen separately from the other reagents for safety reasons. These also require maintaining the gaseous mixture leaving the reactor or recycled thereto outside the limits of inflammability at the pressures and temperatures considered. It is preferable to maintain a so-called rich mixture, that is containing too little oxygen relative to the fuel to ignite. In this regard, the abundant presence (>2%, preferably >5% vol) of hydrogen would constitute a disadvantage given the wide range of inflammability of this compound.

The hydrogen chloride/oxygen ratio used is advantageously between 3 and 6 mol/mol. The ethylene/hydrogen chloride ratio is advantageously between 0.4 and 0.6 mol/mol.

The chlorinated products obtained contain mainly DCE and small quantities of by-products such as 1,1,2-trichloroethane. The separation of the DCE obtained from the stream of products derived from the oxychlorination reactor is carried out according to known modes. The heat of the oxychlorination reaction is generally recovered in vapour form which can be used for the separations or for any other purpose.

The unconverted products such as methane and ethane are then subjected to an easier separation than that which would have been necessary to separate pure ethylene starting from the initial mixture.

The DCE obtained by chlorination or by oxychlorination of ethylene may then be converted to VC.

The invention therefore also relates to a process for the manufacture of VC. To this effect, the invention relates to a process for the manufacture of VC, characterized in that the DCE obtained by the process according to the invention is subjected to pyrolysis.

The conditions under which the pyrolysis may be carried out are known to persons skilled in the art. This pyrolysis is advantageously obtained by a reaction in the gaseous phase in a tubular oven. The usual pyrolysis temperatures are between 400 and 600° C. with a preference for the range between 480° C. and 540° C. The residence time is advantageously between 1 and 60 seconds with a preference for the range from 5 to 25 seconds. The rate of conversion of the DCE is advantageously limited to 45 to 75% in order to limit the formation of by-products and the fouling of the tubes of the oven. The following steps make it possible, using any known device, to collect the purified VC and the hydrogen chloride to be upgraded preferably to the oxychlorination. Following purification, the unconverted DCE is advantageously conveyed to the pyrolysis oven.

In addition, the invention also relates to a process for the manufacture of PVC. To this effect, the invention relates to a process for the manufacture of PVC by polymerization of the VC obtained by the process according to the invention.

The process for the manufacture of PVC may be a mass, solution or aqueous dispersion polymerization process, preferably it is an aqueous dispersion polymerization process.

The expression aqueous dispersion polymerization is understood to mean free radical polymerization in aqueous suspension as well as free radical polymerization in aqueous emulsion and polymerization in aqueous microsuspension.

The expression free radical polymerization in aqueous suspension is understood to mean any free radical polymerization process performed in aqueous medium in the presence of dispersing agents and oil-soluble free radical initiators.

The expression free radical polymerization in aqueous emulsion is understood to mean any free radical polymerization process performed in aqueous medium in the presence of emulsifying agents and water-soluble free radical initiators.

The expression aqueous microsuspension polymerization, also called polymerization in homogenized aqueous dispersion, is understood to mean any free radical polymerization process in which oil-soluble initiators are used and an emulsion of droplets of monomers is prepared by virtue of a powerful mechanical stirring and the presence of emulsifying agents.

The process for the manufacture of DCE according to the invention has the advantage of using two different ethylene fractions which are respectively well suited to the chlorination reaction and to the oxychlorination reaction. In particular, the process according to the invention has the advantage of using an ethylene fraction which is slightly contaminated with hydrogen for the oxychlorination reaction, this being at a cost which is not very high.

Another advantage of this process is that it makes it possible to separate the compounds comprising at least 3 carbon atoms via the fraction C, which compounds are generally responsible for some inhibition during the pyrolysis of the DCE. This inhibition is due to the formation of derivatives such as 1,2-dichloropropane and monochloropropenes. These derivatives are difficult to completely separate from the DCE. Their ease of formation of stable allyl radicals explains their powerful inhibitory effect on the pyrolysis of the DCE which occurs by the free radical route. The formation of these by-products containing three carbon atoms and which are heavier would moreover constitute an unnecessary consumption of reagents during oxychlorination and during chlorination or would result in costs for destruction. Furthermore, these heavy compounds contribute towards the soiling of the columns and the evaporators.

Another advantage of the process according to the invention is that it makes it possible to have, on the same industrial site, a completely integrated process from the hydrocarbon source to the polymer obtained starting with the monomer manufactured.

A final advantage of the process according to the invention is that it would make it possible, by a modification of the conditions for separating the fractions as defined below, to deal with situations where it is advantageous to upgrade an external source of hydrogen chloride, from another manufacturer such as for example a unit for the manufacture of isocyanates. Conversely, it is possible to encounter the situation of an advantageous market for hydrogen chloride which leads to a decrease in the oxychlorination part relative to the chlorination.

BRIEF DESCRIPTION OF THE DRAWINGS

The first embodiment of the process according to the invention will now be illustrated with reference to the drawing accompanying the present description. This drawing consists of the appended FIG. 1, schematically representing one embodiment of the process for the manufacture of DCE according to the invention.

The mixture of products 1 containing ethylene and other constituents resulting from the cracking of a hydrocarbon source is introduced into the main column 2 which is a distillation column equipped with a reboiler at the bottom and a condenser at the top where it is separated into three different fractions, namely fraction 3 which leaves at the top of column 2, which is enriched with compounds lighter than ethylene, in particular methane, hydrogen, nitrogen, oxygen and carbon monoxide and which is conveyed to the chlorination, fraction 4 which leaves at the bottom of column 2 and fraction 5 which is drawn off from the side of the column 2. Fraction 5 is then conveyed to an auxiliary column 6 which is a stripping column equipped with a reboiler, from which is extracted fraction 7 characterized by a very low content of hydrogen which is conveyed to the oxychlorination. The balance of fraction 5 in the form of a stream with a high concentration of impurities more volatile than ethylene 8 is conveyed to the column 2.

Figure 1:
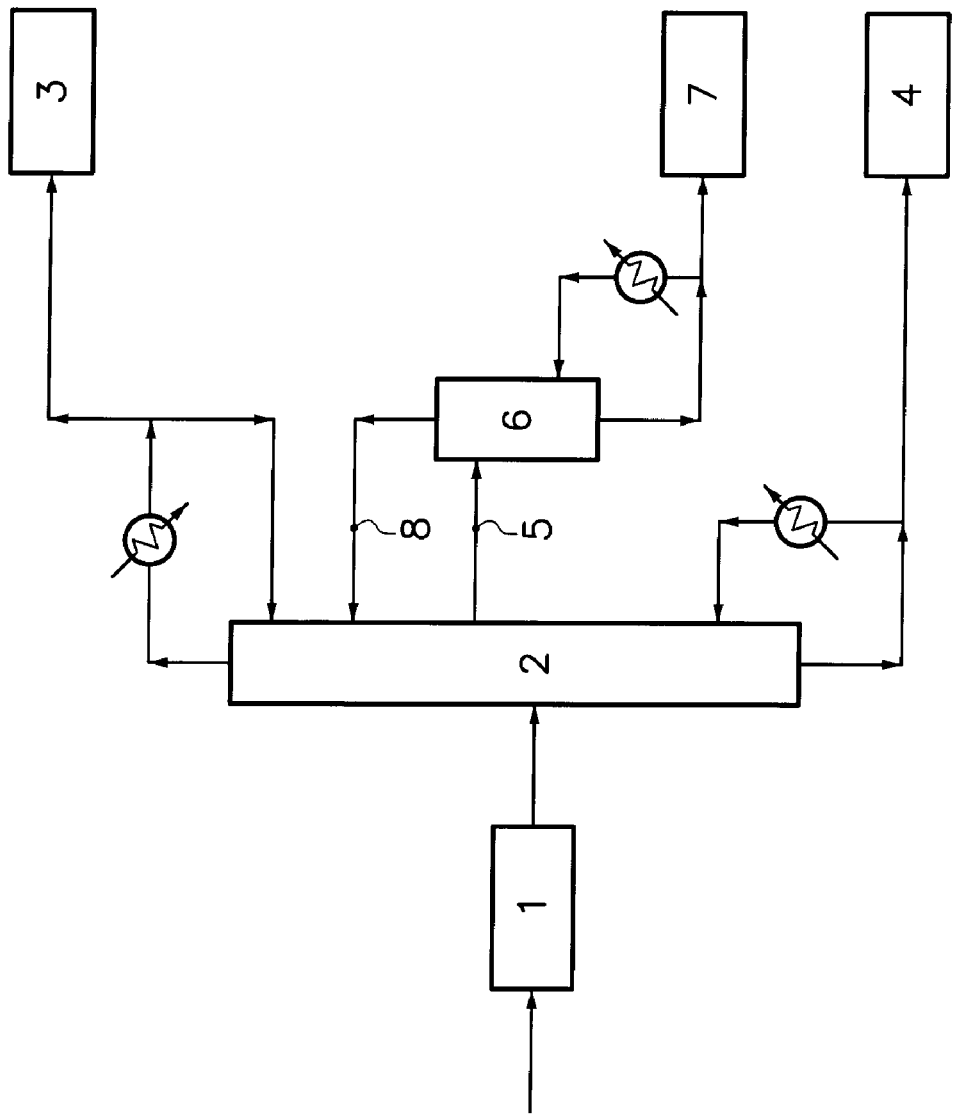
Figure 2:
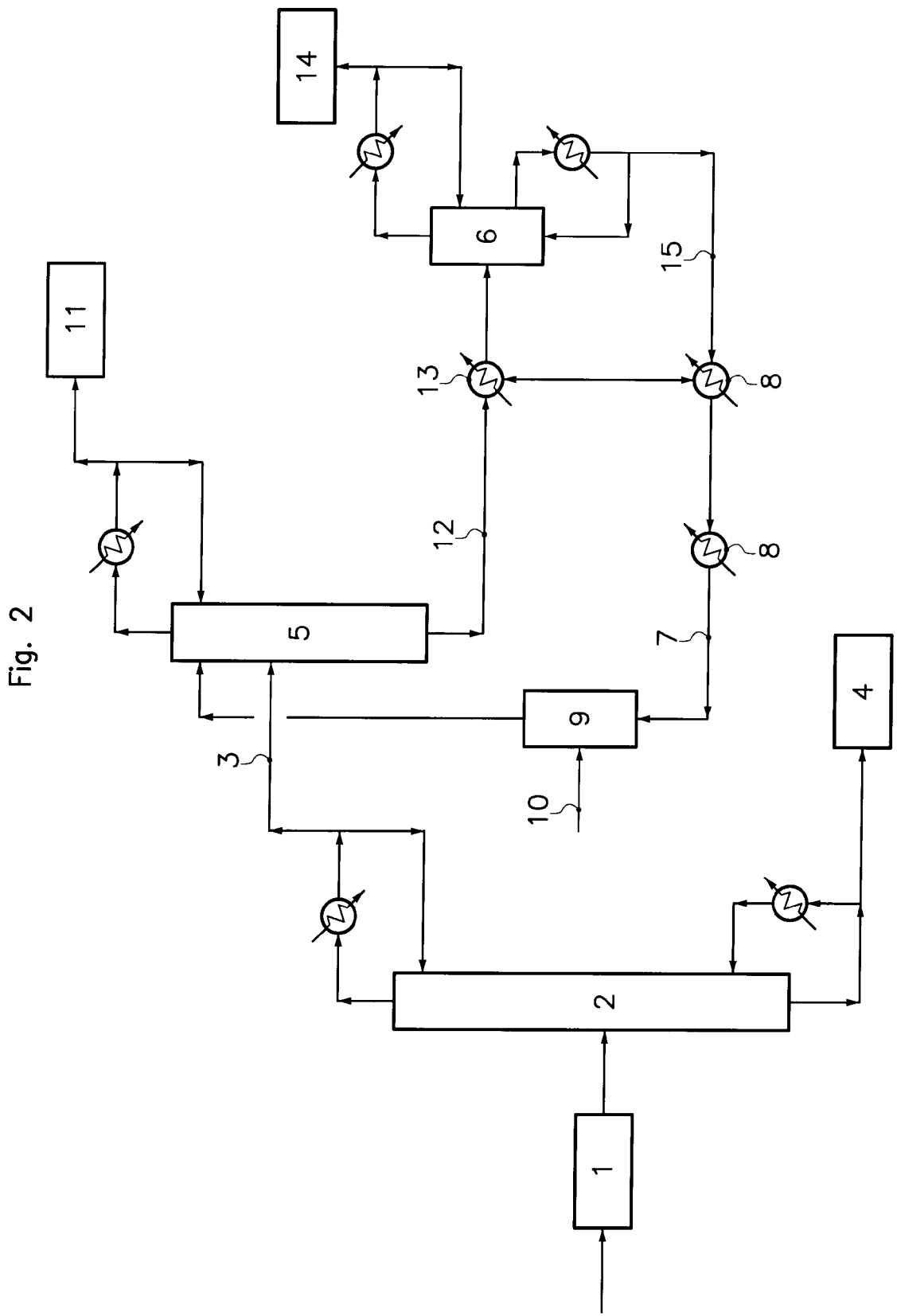

The second embodiment of the process according to the invention will now be illustrated with reference to the drawing accompanying the present description. This drawing consists of the appended FIG. 2, schematically representing one embodiment of the process for the manufacture of DCE according to the invention.

The mixture of products 1 containing ethylene and other constituents resulting from the cracking of a hydrocarbon source is introduced into the main column 2 which is a distillation column equipped with a reboiler at the bottom and a condenser at the top where it is separated into two different fractions, namely fraction 3 at the top of column 2 and fraction 4 at the bottom of column 2.

Fraction 3 is then conveyed to an absorption column 5 equipped with a condenser. Washing agent from the desorption column 6 is introduced into the absorption column 5 via the conduit 7, after having been cooled and put under pressure in the exchangers 8 and the pump 9, respectively. Fresh washing agent is added via the conduit 10 to the washing agent from the column 6.

Following its passage in column 5, fraction 3 is separated into fraction 11 leaving at the top of column 5 and into fraction 12 leaving at the bottom of column 5. Fraction 11, enriched with compounds lighter than ethylene, in particular methane, hydrogen, nitrogen, oxygen and carbon monoxide, is conveyed to the unit for chlorination of ethylene.

Fraction 12, comprising DCE enriched with ethylene, is introduced into the desorption column 6 after having been heated in the exchanger 13.

After its passage in the desorption column 6, equipped with a reboiler at the bottom and a condenser at the top, fraction 12 is separated into fraction 14 leaving at the top of column 6 and into fraction 15 leaving at the bottom of column 6. Fraction 14, characterized by a very low content of hydrogen, is conveyed to the unit for oxychlorination of ethylene. Fraction 15, mainly containing DCE, is conveyed to column 5 via the conduit 7 as explained above.

The exchangers 8 and 13 are coupled in an energy saving perspective.

Figure 3:
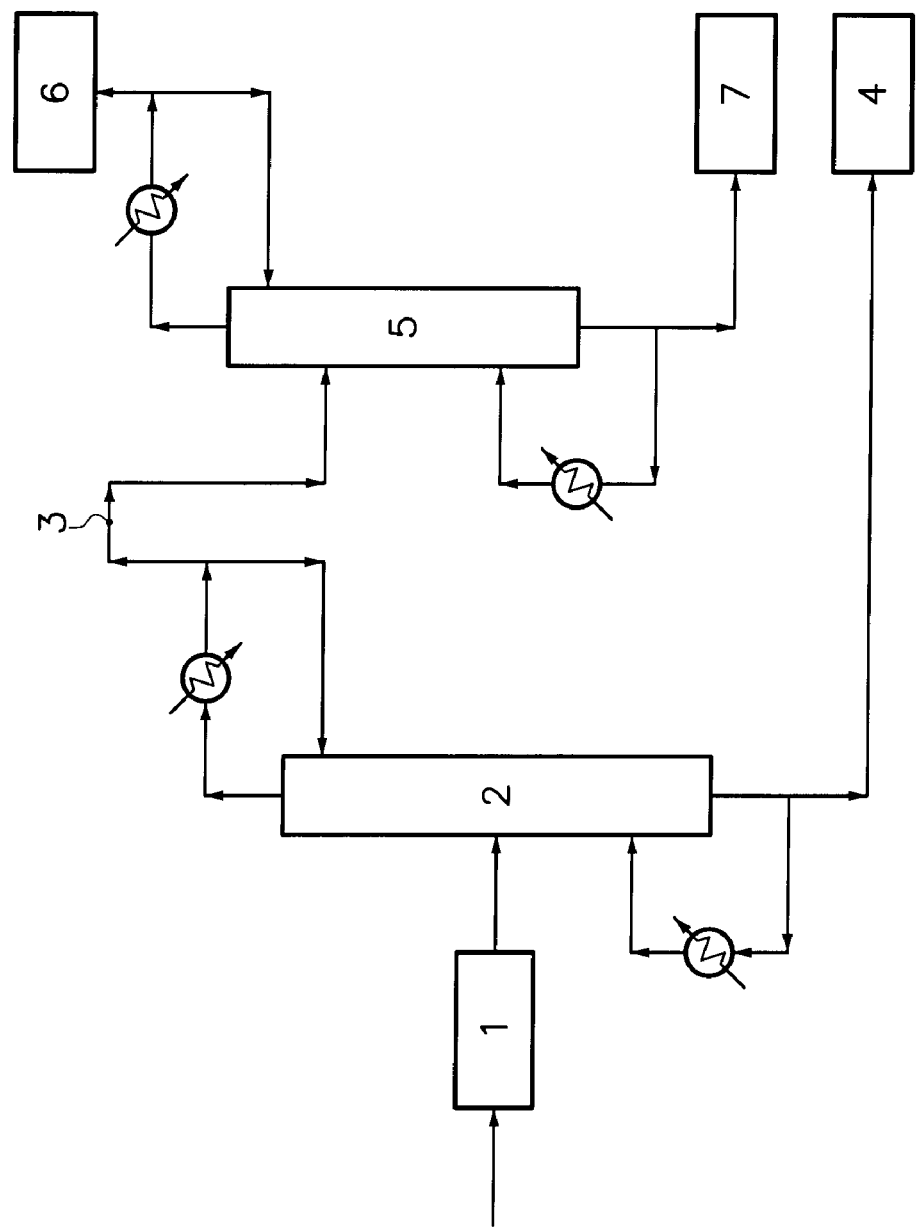

The third embodiment of the process according to the invention will now be illustrated with reference to the drawing accompanying the present description. This drawing consists of the appended FIG. 3, schematically representing one embodiment of the process for the manufacture of DCE according to the invention.

The mixture of products 1 containing ethylene and other constituents resulting from the cracking of a hydrocarbon source is introduced into the main column 2 which is a distillation column equipped with a reboiler at the bottom and a condenser at the top where it is separated into two different fractions, namely fraction 3 at the top of column 2 and fraction 4 at the bottom of column 2.

Fraction 3 is then conveyed to a distillation column 5 equipped with a reboiler at the bottom and a condenser at the top.

Following its passage in column 5, fraction 3 is separated into fraction 6 leaving at the top of column 5 and into fraction 7 leaving at the base of column 5.

Fraction 6, enriched with compounds lighter than ethylene, in particular methane, hydrogen, nitrogen, oxygen and carbon monoxide, is conveyed to the unit for chlorination of ethylene.

Fraction 7, characterized by a very low content of hydrogen, is conveyed to the unit for oxychlorination of ethylene.

Figure 4:
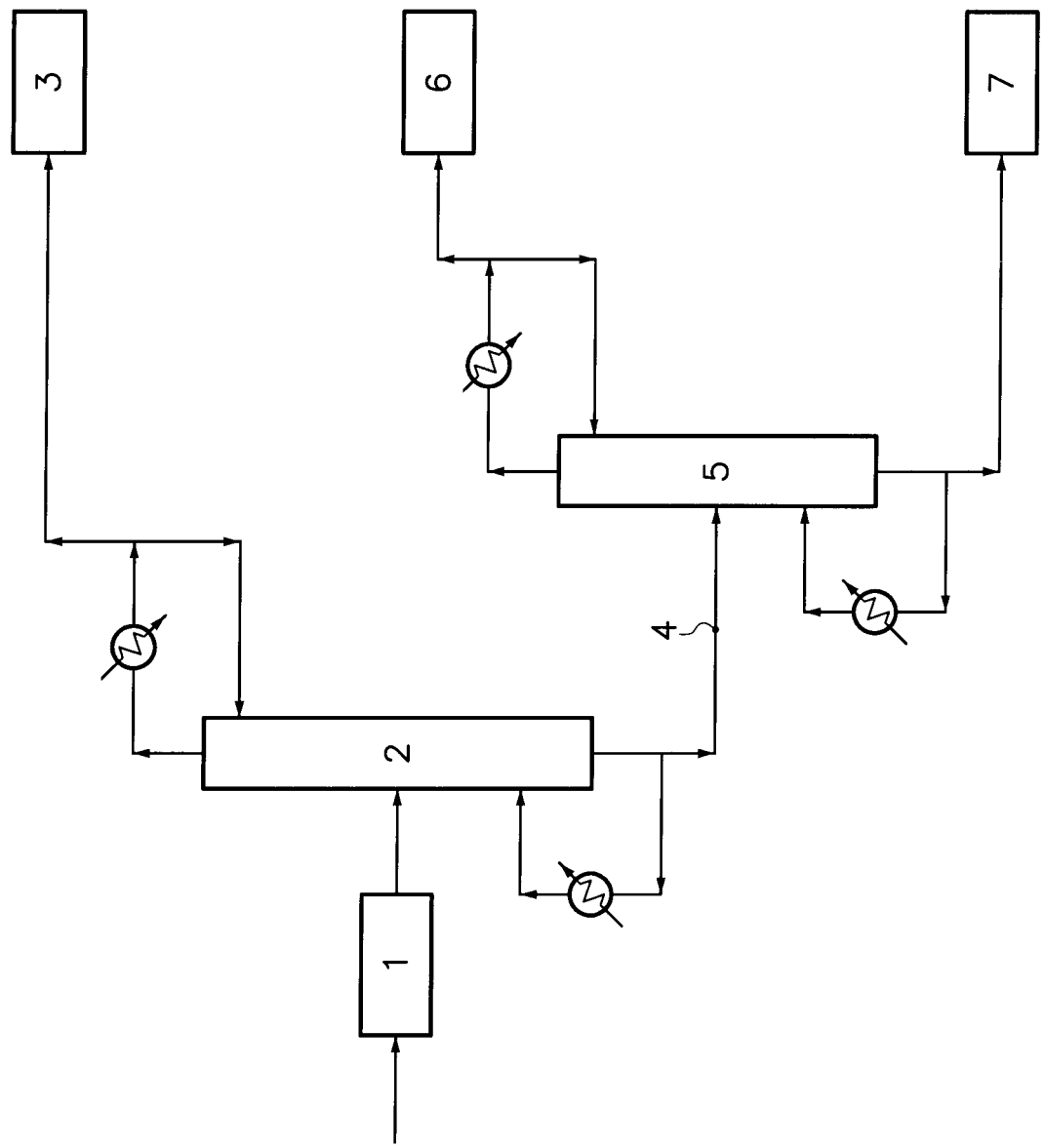

The fourth embodiment of the process according to the invention will now be illustrated with reference to the drawing accompanying the present description. This drawing consists of the appended FIG. 4, schematically representing one embodiment of the process for the manufacture of DCE according to the invention.

The mixture of products 1 containing ethylene and other constituents resulting from the cracking of a hydrocarbon source is introduced into the main column 2 which is a distillation column equipped with a reboiler at the bottom and a condenser at the top where it is separated into two different fractions, namely fraction 3 at the top of column 2 and fraction 4 at the bottom of column 2.

Fraction 3, enriched with compounds lighter than ethylene, in particular methane, hydrogen, nitrogen, oxygen and carbon monoxide, is conveyed to the unit for chlorination of ethylene.

Fraction 4 is then conveyed to a distillation column 5 equipped with a reboiler at the bottom and a condenser at the top.

Following its passage in column 5, fraction 4 is separated into fraction 6 leaving at the top of column 5 and into fraction 7 leaving at the bottom of column 5.

Fraction 6, characterized by a very low content of hydrogen, is conveyed to the unit for oxychlorination of ethylene.

The invention claimed is:

1. A process for the manufacture of 1,2-dichloroethane from a hydrocarbon source comprising:
   a) subjecting the hydrocarbon source to cracking which produces a mixture of products comprising ethylene and other constituents;
   b) separating said mixture of products into a fraction enriched with compounds which are lighter than ethylene (fraction A), comprising part of the ethylene, a fraction enriched with ethylene (fraction B) and a heavy fraction (fraction C);
   c) conveying fraction A to a chlorination reactor and fraction B to an oxychlorination reactor, in which reactors most of the ethylene present in fractions A and B is converted to 1,2-dichloroethane; and
   d) separating the 1,2-dichloroethane from the streams of products derived from the chlorination and oxychlorination reactors.

2. The process according to claim 1, wherein the hydrocarbon source is chosen from the group consisting of naphtha, gas oil, natural gas liquid, ethane, propane, butane, isobutane and mixtures thereof.

3. The process according to claim 1, wherein the hydrocarbon source is chosen from the group consisting of ethane, propane, butane and propane/butane mixtures.

4. The process according to claim 1, wherein the mixture of products comprising ethylene and other constituents derived from a) comprises hydrogen, methane, compounds comprising from 2 to 7 carbon atoms, carbon monoxide, nitrogen and oxygen.

5. The process according to claim 1, wherein fraction B comprises from 40% to 99.5% by volume of ethylene relative to the total volume of fraction B.

6. The process according to claim 1, wherein fraction A comprises a content by volume of ethylene such that it represents from 10% to 90% of the content by volume of ethylene of fraction B.

7. The process according to claim 1, in which b) comprises:
   a first separation S1 comprising the separation of the said mixture of products inside a main column C1 into fraction A at the top of column C1, fraction C at the bottom of column C1 and fraction F1 drawn off from the side of column C1, and
   a second separation step S1' comprising the separation of fraction F1 into a fraction F1' which is conveyed to the column C1 and fraction B.

8. The process according to claim 1, in which b) comprises:
   a first separation S2 comprising the separation of the said mixture of products in a main column C2 into a fraction F2 at the top of column C2 and fraction C at the bottom of column C2,
   a second separation S2' comprising the separation of fraction F2 into fraction A and fraction F2', and
   a third separation S2" comprising the separation of fraction F2' into fraction B and fraction F2".

9. The process according to claim 1, in which b) comprises:
   a first separation S3 comprising the separation of the said mixture of products in a main column C3 into a fraction F3 at the top of column C3 and fraction C at the bottom of column C3, and a second separation S3' comprising the separation of fraction F3 in a column C3' into fraction A at the top of column C3' and fraction B at the bottom of column C3'.

10. The process according to claim 1, in which b) comprises:

a first separation S4 comprising the separation of the said mixture of products in a main column C4 into fraction A at the top of column C4 and fraction F4 at the bottom of column C4, and a second separation S4' comprising the separation of fraction F4 in a column C4' into fraction B at the top of column C4' and fraction C at the bottom of column C4'.

11. The process according claim 1, further comprising converting said 1,2-dichloroethane to vinyl chloride by pyrolysis.

12. The process according to claim 11, further comprising polymerizing said vinyl chloride to polyvinyl chloride.

* * * * *

UNITED STATES PATENT AND TRADEMARK OFFICE
CERTIFICATE OF CORRECTION

PATENT NO. : 7,732,649 B2  Page 1 of 1
APPLICATION NO. : 11/722603
DATED : June 8, 2010
INVENTOR(S) : Michel Strebelle et al.

It is certified that error appears in the above-identified patent and that said Letters Patent is hereby corrected as shown below:

Column 22, Line 49, Claim 7, a second separation "step" S1' comprising the separation of"
should read --a second separation S1' comprising the separation of--

Signed and Sealed this

Twenty-eighth Day of September, 2010

David J. Kappos
*Director of the United States Patent and Trademark Office*